US00PP11662P

United States Patent [19]

van Andel

[11] Patent Number: Plant 11,662

[45] Date of Patent: Nov. 28, 2000

[54] ALSTROEMERIA PLANT NAMED 'STALOREN'

[75] Inventor: Jacob van Andel, Aalsmeer, Netherlands

[73] Assignee: Van Staaveren B.V., Aalsmeer, Netherlands

[21] Appl. No.: 09/226,314

[22] Filed: Jan. 6, 1999

[51] Int. Cl.[7] ..... A01H 5/00

[52] U.S. Cl. ..... Plt./309

[58] Field of Search ..... Plt./309

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed seedlings; namely, 8T935-1 as seed parent and 87G1069-2 as pollen parent. The varietal denomination of the new variety is 'Staloren'.

The first act of asexual reproduction of 'Staloren' was in Aalsmeer, The Netherlands, by propagation by dividing the rhizomes. Asexual reproduction by dividing rhizomes through successive generations in Aalsmeer, The Netherlands, has demonstrated that the combination of characteristics as herein disclosed for 'Staloren' are firmly fixed and retained through successive generations.

SUMMARY OF THE INVENTION

The new variety of Alstroemeria, 'Staloren', produces large flowers.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid as observed in a greenhouse in Aalsmeer, The Netherlands. Color designations indicated are in accordance with The Royal Horticultural Society Colour Chart by color plate designations.

'Staloren' has not been observed under all possible environmental conditions. Phenotypic expression may vary with variations in environment such as temperature, light intensity, day length and growing and cultural conditions.

Botanical classification:

*Family.*—Amaryllidaceae.

*Genus.*—Alstroemeria sp.

Plant:

*Form.*—Bush.

*Shape.*—Upright.

*Height.*—About 150 to 180 cm.

*Main stem.*—About 170 cm.

*Internode length.*—About 1 to 8 cm.

*Growth.*—Vigorous.

*Strength.*—Strong.

*Blooming habit.*—Continuous.

*Rhizomes.*—Plant about 1 to 2 years old. Color: Near 155D. Size: About 10 to 30 cm.

Foliage:

*Number of leaves.*—About 20 to 40 per stem.

*Size of leaf.*—Length: About 15 to 20 cm. Width: About 3 to 5 cm.

*Shape of leaf.*—Elliptic.

*Margin.*—Straight, entire.

*Texture.*—Glossy.

*Color.*—Upper side: Near 137A. Underside: Near 137C.

Flower:

*Size* (*when first anthers release pollen*).—Diameter: About 7 cm. Depth: About 5 cm.

*Borne.*—About 3 to 6 flowers per umbel.

*Shape or form.*—When bloom first opens: Cup. When bloom matures: Cup.

*Fragrance.*—None.

*Lasting quality.*—On plant: About 4 weeks. As cut flower: About 16–18 days.

*Tepalage.*—Number of tepals: About 6. Arrangement: 2 concentric circles of 3 tepals. Shape: Obovate. Margin: Minutely crimped. Apex: Pointed. Texture: Soft. Appearance: Velvety.

*Color.*—Outer tepals — Upperside body near 29C and 46C distally, base near 2D, no spots, underside near 29C and 46C distally. Inner median tepal — Near 29C and 6C with near 46C on distal end, base near 2D, about 20–30 spots, near 185A, underside near 29C and 6C with near 46C on distal end. Inner lateral tepals — Body near 29C with large area of about 6A as illustrated with near 46C distally, base near 2D, about 20–40 spots, near 185A, underside near 29C with area of 6A and 49C similar to tepal upper surface. General: Inner tepal long obovate, outer tepal obovate.

Flower stem:

*Peduncle length.*—About 10 to 15 cm. Color: Near 137B. Strength: Strong, upright. Discoloration: No discoloration after full bloom, not hairy.

*Persistence.*—Flower does not hang on and dry.

*Disease resistance.*—Unknown.

Bud:

*Size.*—Diameter: About 1 to 2 cm. Depth or length: About 2 to 4 cm.

*Form.*—Pear-shaped.

*Rate of opening.*—Fast.

*Color of tepals when tepals first divide.*—Near 29B and 46C.

*Color of tepals when tepals begin to unfurl.*—Near 29B and 46C.

Reproductive organs:

*Stamen.*—Number: About 6. Arrangement: Side by side around the style.

*Anthers.*—Size: About 8 to 10 mm. Color: Near 148A.

*Filaments.*—Length: 5 cm. Color: Near 29C.

*Pollen.*—Color: Near 166A.

*Pistils.*—1. Styles: Length about 4 to 5 cm. Color: Near 29C.

*Stigmas.*—Color: Near 43C.

Fruit: Fertile.

*Shape.*—Round.

*Color at maturity.*—Near 163A.

I claim:

1. A new and distinct Alstroemeria plant of the variety substantially as shown and described.

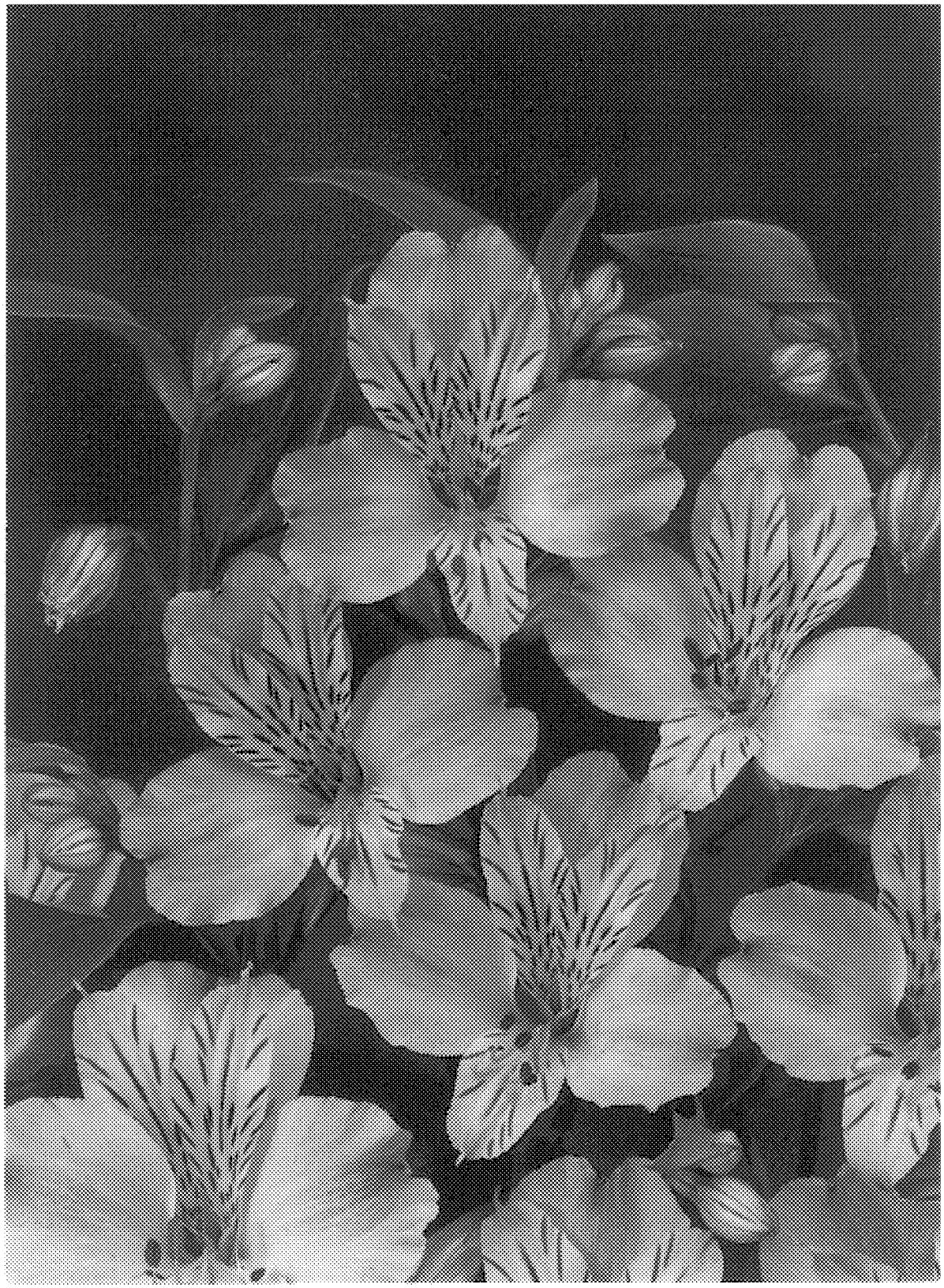

* * * * *